(12) United States Patent
van Oudenallen et al.

(10) Patent No.: US 9,956,112 B2
(45) Date of Patent: May 1, 2018

(54) PREWARMING GOWN

(75) Inventors: Robertus Gerardus van Oudenallen, Vleuten (NL); Berend Jan Teunissen, Haaksbergen (NL)

(73) Assignee: THE SURGICAL COMPANY INTERNATIONAL B.V., Amersfoort (NL)

( * ) Notice: Subject to any disclaimer, the term of this patent is extended or adjusted under 35 U.S.C. 154(b) by 1705 days.

(21) Appl. No.: 13/220,383

(22) Filed: Aug. 29, 2011

(65) Prior Publication Data

US 2012/0047623 A1  Mar. 1, 2012

Related U.S. Application Data

(60) Provisional application No. 61/378,245, filed on Aug. 30, 2010.

(51) Int. Cl.
*A61F 7/00* (2006.01)
*A61F 7/02* (2006.01)

(52) U.S. Cl.
CPC .............. *A61F 7/0085* (2013.01); *A61F 7/02* (2013.01); *A61F 7/0097* (2013.01);
(Continued)

(58) Field of Classification Search
CPC .............. A41D 13/012; A41D 13/0125; A41D 13/0155; A41D 13/12; A41D 13/1209; A41D 13/1263; A41D 13/1281; A41D 13/00; A41D 13/002; A41D 13/0025; A41D 13/005; A41D 13/0053; A41D 13/0051;
(Continued)

(56) References Cited

U.S. PATENT DOCUMENTS 302,901 A * 8/1884 Fenne ............................... 2/114
459,106 A * 9/1891 Fifield ............................... 2/114
(Continued)

FOREIGN PATENT DOCUMENTS

JP  59-047614 U  3/1984

OTHER PUBLICATIONS

International Search Report (ISR) and Written Opinion (WO) for the International PCT Application No. PCT/EP2011/064878, dated Oct. 31, 2011.
(Continued)

*Primary Examiner* — Alissa L Hoey
(74) *Attorney, Agent, or Firm* — Nixon & Vanderhye P.C.

(57) ABSTRACT

A device for warming a human body. The device is a gown that has a body with a thorax portion and a leg portion. One embodiment prevents redistribution hypothermia with a distributor attached to the inside of the leg portion. The sleeves, leg portion, and posterior of the gown are heat reflective. The anterior of the thorax portion of the gown is non-reflective. The distributor inflates when heated air is supplied. The distributor exhausts air into the gown. Temperature is maintained at a desired level for the extremities, while preventing the thorax area from being elevated to an uncomfortable level. Another embodiment is a perioperative warming device. The device is a gown that has a thorax portion and a leg portion. Each portion has an independent air chamber and inlet. The two portions are releasably connected. The sleeves, leg portion, and anterior of the gown are heat reflective.

15 Claims, 8 Drawing Sheets

(52) U.S. Cl.
CPC . *A61F 2007/006* (2013.01); *A61F 2007/0234* (2013.01); *A61F 2007/0236* (2013.01); *A61F 2007/0257* (2013.01); *A61F 2007/0258* (2013.01)

(58) Field of Classification Search
CPC ............ A41D 2400/10; A41D 2400/12; A41D 2400/14; A62B 17/00
USPC .................... 2/114, 67, 82, 89, 269, 69, 901
See application file for complete search history.

(56) References Cited

U.S. PATENT DOCUMENTS

| | | | | |
|---|---|---|---|---|
| 695,496 | A * | 3/1902 | Schermerhorn | 2/114 |
| 818,351 | A * | 4/1906 | Clark | 2/114 |
| 956,102 | A * | 4/1910 | Jones | 2/114 |
| 1,462,515 | A * | 7/1923 | McElroy | 2/72 |
| 1,489,046 | A * | 4/1924 | Thompson | 2/114 |
| 1,547,085 | A * | 7/1925 | Tucker | 2/69.5 |
| 1,766,272 | A * | 6/1930 | Vallier | 2/114 |
| 3,307,554 | A * | 3/1967 | Thornton | 607/107 |
| 4,811,429 | A * | 3/1989 | Perez | 2/83 |
| 4,945,924 | A * | 8/1990 | Poettgen | 128/849 |
| 5,062,159 | A * | 11/1991 | Jakub | 2/114 |
| 5,088,117 | A * | 2/1992 | Fulmer | 2/114 |
| 5,123,120 | A * | 6/1992 | Ross | 2/229 |
| 5,133,086 | A * | 7/1992 | Truitt et al. | 2/114 |
| D336,968 | S * | 7/1993 | Russano | D2/720 |
| 5,405,370 | A * | 4/1995 | Irani | 607/104 |
| 5,440,763 | A * | 8/1995 | Shah et al. | 2/114 |
| 5,628,064 | A * | 5/1997 | Chung | 2/70 |
| 5,866,881 | A * | 2/1999 | Jones, III | 219/527 |
| 5,893,991 | A * | 4/1999 | Newell | 219/211 |
| 5,970,519 | A * | 10/1999 | Weber | 2/81 |
| 5,977,517 | A * | 11/1999 | Grosjean | 219/211 |
| 6,049,062 | A * | 4/2000 | Jones | 219/211 |
| 6,578,217 | B1 | 6/2003 | Roberson | |
| 6,649,873 | B1 * | 11/2003 | Cintron et al. | 219/211 |
| D495,468 | S * | 9/2004 | Wheeler-Dickson et al. | D2/720 |
| 6,883,185 | B2 | 4/2005 | Duncan | 2/458 |
| 7,001,416 | B2 | 2/2006 | Augustine et al. | |
| 7,093,304 | B2 * | 8/2006 | Griesbach, III | 2/83 |
| 7,101,389 | B1 | 9/2006 | Augustine et al. | |
| 7,107,629 | B2 * | 9/2006 | Miros et al. | 2/458 |
| D530,885 | S * | 10/2006 | Barthel | D2/720 |
| 7,226,454 | B2 | 5/2007 | Albrecht et al. | |
| 7,276,076 | B2 | 10/2007 | Bieberich | |
| 7,364,584 | B2 | 4/2008 | Anderson | |
| 7,470,280 | B2 | 12/2008 | Bieberich | |
| 7,837,721 | B2 * | 11/2010 | Augustine et al. | 607/96 |
| 8,011,019 | B1 * | 9/2011 | Hamid et al. | 2/69 |
| 8,465,351 | B2 * | 6/2013 | Smith et al. | 454/370 |
| 8,597,339 | B2 * | 12/2013 | Augustine et al. | 607/108 |
| 2002/0042640 | A1 | 4/2002 | Augustine et al. | |
| 2004/0040087 | A1 * | 3/2004 | Lack et al. | 5/413 AM |
| 2004/0078864 | A1 * | 4/2004 | Miros et al. | 2/69 |
| 2004/0088774 | A1 * | 5/2004 | Lawson | 2/69 |
| 2005/0143796 | A1 | 6/2005 | Augustne et al. | |
| 2005/0178138 | A1 * | 8/2005 | Blackstone | 62/259.3 |
| 2006/0047332 | A1 | 3/2006 | Malmberg et al. | |
| 2006/0052853 | A1 | 3/2006 | Augustine et al. | |
| 2006/0070162 | A1 * | 4/2006 | Frank | 2/69 |
| 2006/0080756 | A1 * | 4/2006 | Goldfine | 2/102 |
| 2006/0117456 | A1 * | 6/2006 | Griesbach, III | 2/114 |
| 2006/0135016 | A1 | 6/2006 | Iwasaki | |
| 2006/0174392 | A1 * | 8/2006 | Farnworth et al. | 2/102 |
| 2006/0184217 | A1 | 8/2006 | Van Duren | |
| 2006/0213895 | A1 * | 9/2006 | Dennis | 219/211 |
| 2006/0259104 | A1 | 11/2006 | Panser et al. | |
| 2007/0093882 | A1 | 4/2007 | Anderson | |
| 2007/0118952 | A1 * | 5/2007 | Lee | 2/69 |
| 2007/0157651 | A1 * | 7/2007 | Naaman | 62/259.3 |
| 2007/0208397 | A1 * | 9/2007 | Gardner | 607/88 |
| 2007/0239239 | A1 | 10/2007 | Albrecht et al. | |
| 2008/0027521 | A1 | 1/2008 | Bieberich | |
| 2008/0027522 | A1 | 1/2008 | Beiberich | |
| 2008/0125840 | A1 | 5/2008 | Anderson | |
| 2008/0177361 | A1 | 7/2008 | Anderson | |
| 2009/0044308 | A1 * | 2/2009 | Hsieh | 2/69 |
| 2009/0044932 | A1 * | 2/2009 | Blackstone | 165/158 |
| 2009/0062891 | A1 | 3/2009 | Bieberich | |
| 2009/0149931 | A9 | 6/2009 | Anderson | |
| 2009/0181610 | A1 * | 7/2009 | Duke | 454/241 |
| 2009/0228083 | A1 | 9/2009 | Anderson | |
| 2009/0271917 | A1 * | 11/2009 | Richardson | 2/458 |
| 2010/0179624 | A1 | 7/2010 | Anderson et al. | |
| 2010/0242147 | A1 * | 9/2010 | Pohr et al. | 2/69 |
| 2010/0282433 | A1 | 11/2010 | Blackford | |
| 2011/0009930 | A1 * | 1/2011 | Officier et al. | 607/104 |
| 2011/0022135 | A1 * | 1/2011 | Augustine et al. | 607/104 |
| 2012/0005803 | A1 * | 1/2012 | Sagami | 2/114 |
| 2012/0047622 | A1 * | 3/2012 | van Oudenallen | 2/81 |
| 2012/0305541 | A1 * | 12/2012 | Giles et al. | 219/211 |
| 2013/0104277 | A1 * | 5/2013 | McCue | 2/69 |
| 2013/0104279 | A1 * | 5/2013 | Galli et al. | 2/69 |
| 2013/0231723 | A1 | 9/2013 | Van Oudenallen | |
| 2013/0239288 | A1 * | 9/2013 | Van Duren | 2/69 |

OTHER PUBLICATIONS

U.S. Appl. No. 13/819,498, filed Apr. 18, 2013.
Sep. 22, 2016 Office Action issued in U.S. Appl. No. 13/819,498 citing US 2010/0282433.

* cited by examiner

PREWARMING GOWN

CROSS-REFERENCE TO RELATED APPLICATIONS

This application claims the benefit of U.S. Provisional Application No. 61/378,245, filed Aug. 30, 2010.

STATEMENT REGARDING FEDERALLY SPONSORED RESEARCH OR DEVELOPMENT

Not Applicable

BACKGROUND

1. Field of Invention

This invention relates to a system for warming the body of a human. More particularly, this invention pertains to passive warming and active warming before, during, and after surgery or other medical procedures.

2. Description of the Related Art

Inflatable thermal blankets that are used to communicate a conditioned gas, such as heated or cooled air, to a patient are known in the art. Such thermal blankets typically have an inflatable portion provided with an inlet port for placing the inflatable portion in fluid communication with a source of pressurized, conditioned gas such that the inflatable portion can be selectively inflated. The inflatable portion generally has an inner surface that is positioned next to the patient. The inner surface is gas permeable or is otherwise adapted to communicate the conditioned gas used to inflate the blanket to the user. The warm air used to inflate the inflatable portion is communicated through the inner surface of the inflatable portion so as to bath the body portion covered by the blanket in warm air.

Warming devices for perioperative use are also known. For example, U.S. Pat. No. 7,276,076, issued on Oct. 2, 2007, to Bieberich and titled "Perioperative warming device," discloses a warming device for perioperative use. The warming device includes a gown and convective apparatus on the inside of the gown. Each convective apparatus has a pair of outer sheets separated by an air-impermeable layer. The air-impermeable layer is a barrier separating the sections. Air inlets are provided for each section.

Another example is U.S. Pat. No. 7,364,584, issued on Apr. 29, 2008, to Anderson and titled "Warming device," discloses warming device that is a garment with a convective apparatus with interleaved, separately inflatable sections inside the garment. The convective apparatus has two sections that are each separately inflatable. One section is comb-shaped and provides therapeutic warming to the patient. The other section interleaves with the first section and provides comfort warming to the patient.

BRIEF SUMMARY

According to one embodiment of the present invention, a device for warming a patient that includes a gown having a body that includes an air distributor and heat reflective and non-heat reflective portions. The body includes a thorax portion and a leg portion. The thorax portion encloses the patient torso and includes a back portion made from two flaps. The sleeves extend from the body and enclose the arms. The leg portion encloses the legs down to the ankles. The leg portion includes a drape that is releasably attached to the leg portion. The drape in detached form is extendable to cover the patient's feet. The device includes a distributor attached to the inside of the leg portion. The distributor allows for air to flow through the distributor and throughout the inside of the gown.

The sleeves, leg portion, and back portion of the gown include a heat reflective material. The anterior of the thorax, or chest, portion of the gown is non-reflective. In one embodiment, the fabric of the gown is bio-degradable.

The distributor is connectable to an air hose. The distributor inflates when forced, heated air is supplied and pushes the heated air throughout the inside of the gown. Air temperature is maintained at a desired level for the extremities, while also preventing the chest or thorax area from being increased to an uncomfortable level. The air temperature of the patient can be maintained within the gown before, during, or after surgery or any other medical procedure.

In such an embodiment as described above, the prewarming gown heats the limbs to prevent redistribution hypothermia and for optimal heat storage in the patient's body. Forced air heated full body blankets are very effective in warming the limbs. However, no distinction is made to the thorax and the limbs. The heat flow to the thorax can lead to an increase of the core temperature and a reduction of comfort, and thus sweating. Furthermore, patient mobility is restricted by full body blankets. The disclosed prewarming system operates to reduce the core-to-peripheral temperature gradient to prevent redistribution hypothermia, and also to increase the heat content of peripheral compartments (heat accumulation) to compensate for the heat loss during anesthesia.

The prewarming system includes a full body gown, integrated tube shape flow distributor, a blower, and a corrugated hose. The gown combines passive insulation by reflective fabric with forced air warming. The combination of reduced heat loss and active heat supply results in an increase of the peripheral compartment's heat content and temperature.

Heat is supplied by heated forced air which is created in the blower. From the blower the heated, forced air is transferred to the gown via a corrugated hose. The heated forced air enters the gown in the leg portion. From the leg portion, the heated air is transferred partly to the feet and partly to the upper body. The heated air flows along the body and leaves the gown at the feet, at the neck opening, and at the sleeves.

Medical requirements for the gown prescribe that the heated air flowing through the gown must be above 36° C. to prevent hypothermia. Heated forced air is created in a compact blower with a high rpm fan and a heat exchanger. To prevent unintended cooling of the patient, the output temperature of the blower is adjusted to a range of 36-43° C. The patient can adjust the output volume flow of the blower manually to a comfortable level. The compact blower is supplied with a bed mounting mechanism. By means of an optional battery pack, the blower can be kept in operation while the patient is transported.

The gown is supplied with a horizontal slit at the front side at lower leg level. The corrugated hose is connected through the slit to a flow distributor integrated in the gown. The integrated flow distributor includes an inflatable tube. In one embodiment, the distributor includes perforations. In another embodiment, the distributor is made from air permeable fabric, such as melt blown polypropylene.

The gown includes an extendable piece of fabric which is optionally draped over the feet for insulation or be flipped back and secured to the gown. In some embodiments, the extendable piece of fabric is secured by a hook and loop fastener system, tape, or ropes in such a way that the patient can walk while wearing the gown.

The fabric of the gown is supplied with a reflective coating (such as alumina) at the arms, legs, and back to reduce the heat loss by radiation. The fabric at the thorax is uncoated to reduce the increase in core temperature due to the supplied heated air.

The prewarming system distinguishes itself from other prewarming systems in effective heating of the legs and arms while maintaining a constant core temperature. Furthermore, the patient's freedom of movement is not restricted as with heated mattresses and blankets. Besides prewarming, the gown provides patient warming during surgery and during postoperative warming. The seam at the back portion of the gown is openable such that the gown can be draped more optimally during treatment.

In another embodiment, the prewarming gown is a perioperative device with an upper body portion and a removable lower body portion. The upper body portion has two layers. The inside layer is an air permeable sheet that is attached to the inside surface of the outer layer to form an upper air chamber therebetween. The outer layer where proximate the inside layer is air impermeable. The upper air chamber has an inlet allowing connection of an air hose. In one embodiment, the upper body portion has sleeves that are separable into a distal sleeve and a medial sleeve.

The lower body portion is made of two sheets. The inner sheet is air permeable and is attached to the outer sheet to form a lower air chamber. The outer layer where proximate the inside layer is air impermeable. The lower air chamber has an inlet allowing connection of an air hose.

The upper body portion and the lower body portion are joined to form a long gown. With the lower body portion removed from the upper body portion, each is usable separably. In one embodiment the connection between the upper and lower body portions is made with a hook and loop fastener system. In this way the lower body portion is releasably attachable to the upper body portion.

In one embodiment, the outer layers have portions that are heat reflective. In one such embodiment, the sleeves and the anterior of the upper and lower body portions are heat reflective. In one such embodiment, the posterior of the upper and lower body portions are air permeable to allow escape of the air released from the upper and lower air chambers.

BRIEF DESCRIPTION OF THE SEVERAL VIEWS OF THE DRAWINGS

The above-mentioned features will become more clearly understood from the following detailed description read together with the drawings in which.

The above-mentioned features will become more clearly understood from the following detailed description read together with the drawings in which.

DETAILED DESCRIPTION

A gown 100, 1500 for warming a patient is disclosed. The gown 100, 1500 provides passive warming and active warming of patients before, during, and/or after surgery or other medical procedures. In one configuration, the gown 100 prevents redistribution hypothermia and in another configuration the gown 1500 is suitable for perioperative use. The gown 100, 1500 is intended to be worn by a human 102. For ease in identifying locations, the various anatomical terms of location are used. For example, the superior-inferior axis coincides with the axis from the neck area to the foot area of the gown 100, 1500. The transverse plane is perpendicular to the superior-inferior axis.

Figure 1:
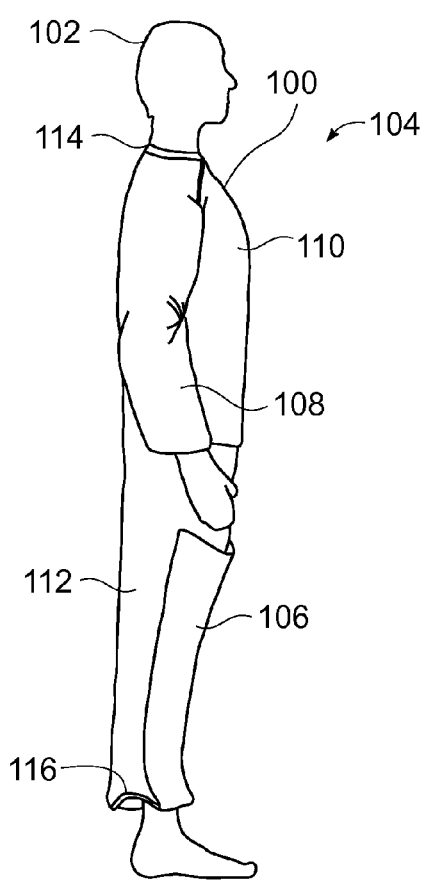
FIG. 1 is a side view of one embodiment of a warming gown on a standing patient.
Figure 2:
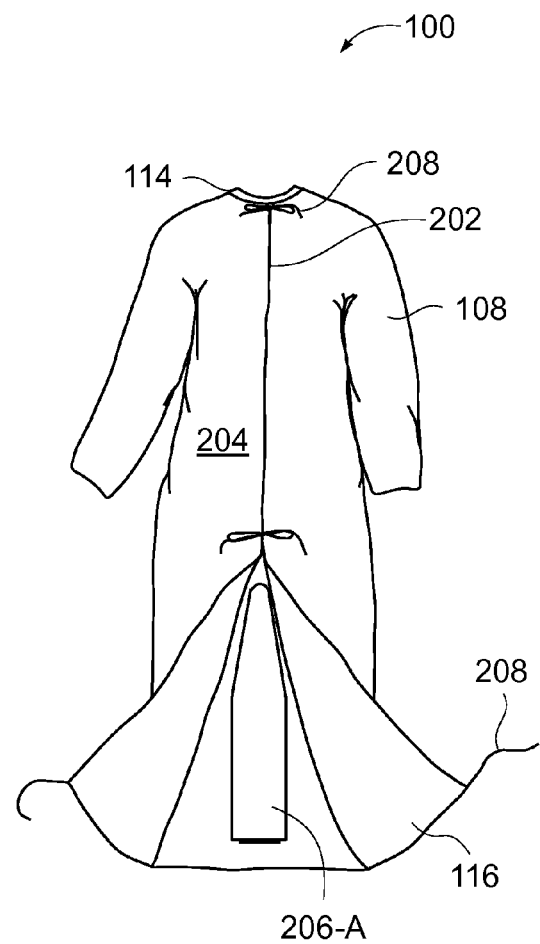
FIG. 2 is a rear view of the warming gown of FIG. 1.

FIG. 1 illustrates a side view of one embodiment of a gown 100 worn by a patient 102 who is standing. FIG. 2 illustrates a rear view of the gown 100. FIGS. 1 and 2 show the gown 100 in a first, or passive, configuration that is suitable for a patient 102 who is mobile. The passive configuration allows the patient 102 to stand, walk, sit, or otherwise move or position himself.

The gown 100 includes a body 104, a drape 106, and a pair of sleeves 108. The body 104 has a thorax portion 110 and a leg portion 112. The thorax portion 110 is sized and configured to fit loosely around the thorax of the patient 102. The thorax portion 110 encloses the torso of the patient 102 by encircling the patient's body. The thorax portion 110 has an opening 114 through which the neck of the patient 102 extends. With the patient 102 upright, such as when standing or sitting, the gown 100 is supported by the thorax portion 110 of the gown 100 resting on the shoulders of the patient 102.

The leg portion 112 extends distally toward the feet of the patient 102. In the illustrated embodiment, the leg portion 112 extends as far as the ankles of the patient 102. The feet of the patient 102 extend through an opening in the leg portion 102. The opening is defined by a hem 116, which is the edge of the leg portion 102. The leg portion 112 encloses a portion of the lower extremities of the patient 102 without hindering the mobility of the patient 102 when he is walking or otherwise moving about.

The proximal end of the drape 106 is attached to a portion of the hem 116 of the leg portion 112 of the gown 100. The drape 106 is illustrated in the stored position with the distal end of the drape 106 secured to the gown 100. In other embodiments the drape 106 is folded, rolled, or otherwise stowed in the stored position. In this way the drape 106 does not extend below the hem 116 of the leg portion 112 in a manner that poses a tripping hazard to the patient 102 nor does the drape 106 hinder the mobility of the patient 102.

The pair of sleeves 108 extend from the body 104 of the gown 100. In one embodiment, the sleeves 108 have a length that is sufficient to enclose the arms of the patient 102 from the shoulders to the wrists of the patient 102. In another embodiment, the sleeves 108 have a longer length that is sufficient to also enclose the hands of the patient 102. In such an embodiment, the hands, including the fingers of the patient 102, are contained inside the sleeves 108 and subject to the warming effects of the gown 100.

The gown 100 encloses a substantial portion of the body of the patient front to back. The gown 100 has a posterior opening 202 that extends from the neck opening 114 to the hem 116 of the leg portion 112. The posterior opening 202 is formed from a pair of flaps 204. The pair of flaps 204 are the posterior portion of the gown 100 and extend from the neck opening 114 to the hem 116 of the leg portion 112. The posterior opening 202 is partially closed by joining the edges of the pair of flaps 204 at one or more locations. In one embodiment, the flaps 204 are joined or connected by straps 208, on each flap 204. A first pair of straps 208 closes the neck opening 114 of the gown 100, and a second pair of straps 208 closes a second location medial to the gown 100. In other embodiments, the flaps 204 are joined or connected by string, buttons, snaps, hook and loop fasteners, and/or connectors that releasably secure the flaps 204 together.

Inside the gown 100 and attached to the inside, anterior surface of the leg portion 112 is a distributor 206-A. The distributor 206-A is positioned such that it is generally between where the legs of the patient 102 contact the leg portion 112 when the patient 102 is standing with feet at shoulder width apart. The distributor 206-A has a distal end that extends towards the crotch of the patient 102. In the illustrated configuration the distributor 206-A is deflated and rests substantially next to the leg portion 112. In this way the patient 102 is not hindered by the distributor 206-A. In another embodiment, the distributor 206-A is a sheet of an air permeable material that is attached to the lower or leg portion 112 of the gown 100. The sheet of air permeable material and the gown 100 define a chamber that receives treated air and distributes that air to the legs and lower body of the patient 102.

In one embodiment, the gown 100 is made of a nonwoven material that is air permeable, such as polypropylene. In one such embodiment, the material is bio-degradable. The drape 106, the sleeves 108, the leg portion 112, and the posterior portion of the body 104 include a material that is heat reflective. This heat reflective material provides passive warming when heated air is forced into those portions of the gown 100. The anterior thorax portion 110 does not include the heat reflective material. The heat reflective material has a low emissivity such that the heat proximate the patient 102 is not substantially reflected or radiated away from the patient 102, which tends to prevent cooling of the patient 102 by heat radiation losses.

Figure 3:
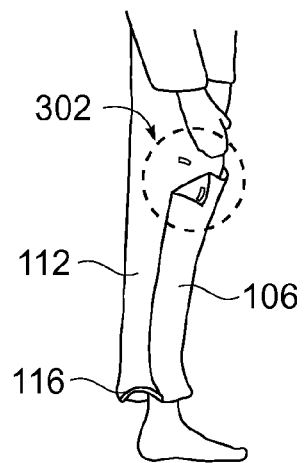
FIG. 3 is a side view of one embodiment for fastening a drape to the warming gown of FIG. 1.

FIG. 3 illustrates a side view of one embodiment for fastening the drape 106 to the leg portion 112 of the gown 100. In the illustrated embodiment, the drape 106 is stowed in the stored position with the gown 100 in a vertical position. In the stored position, the proximal end of the drape 106 is attached to a portion of the hem 116 of the leg portion 112 of the gown 100, and the distal end of the drape 106 is secured via fasteners 302 to the leg portion 112 of the gown 100.

In the illustrated embodiment, the fasteners 302 are hook and loop fasteners. In other embodiments, the drape 106 is secured by straps, string, buttons, snaps, and/or connectors that releasably secure the drape 106 to the leg portion 112. With the drape 106 secured to the leg portion 112 of the gown 100, the drape 106 does not extend below the hem 116 of the leg portion 112 in a manner that poses a tripping hazard to the patient 102, and increased mobility is available to the patient 102.

Figure 4:
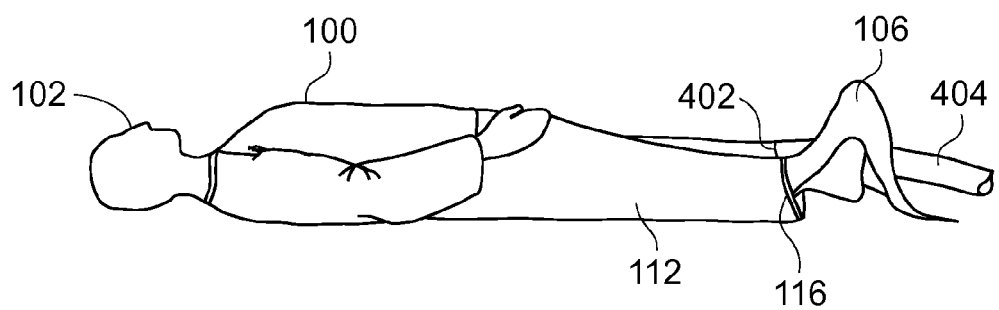
FIG. 4 is a side view of one embodiment of the warming gown on a supine patient.
Figure 5:
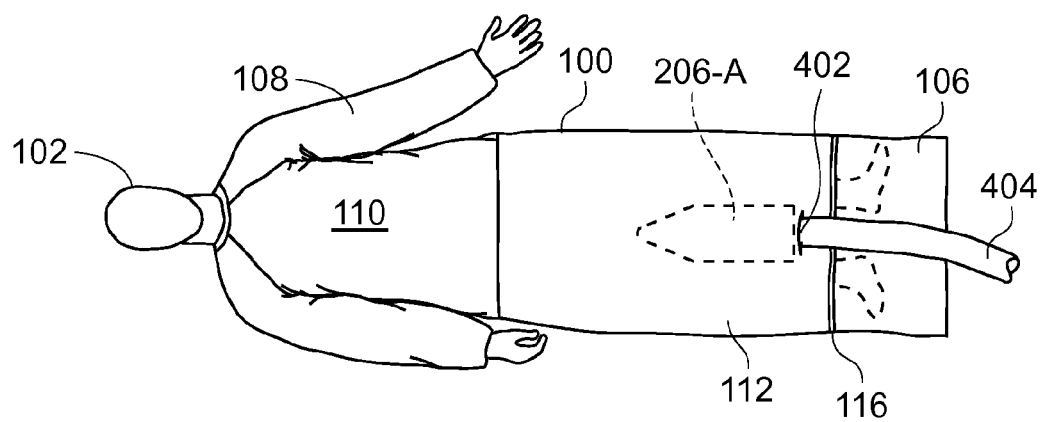
FIG. 5 is a top view of the warming gown of FIG. 4.

FIG. 4 illustrates a side view of the gown 100 worn by a patient 102 who is supine, such as someone who is on a gurney. FIG. 5 illustrates a top view of the gown 100. FIGS. 4 and 5 show the gown 100 in a second, or active, configuration that is suitable for a patient 102 who is supine, prone, or in Fowler's position, that is, sitting with legs extended. In the active configuration, the patient's mobility is restricted primarily to limited positioning of himself and to circumstances where the patient 102 is transported on gurneys and such like.

The gown includes a body 104, a drape 106, and a pair of sleeves 108. The body has a thorax portion 110 and a leg portion 112. In the supine position, the thorax portion 110 is supported by the highest portion of the patient's body. In a supine position, the thorax portion 110 hangs from the chest and the neck of the patient 102. Since the thorax portion 110 encircles the torso, a supine patient 102 is positioned horizontally above the inside, posterior portion of the gown 100.

The pair of sleeves 108 extend from the body 104 of the gown 100. In one embodiment, the sleeves 108 have sufficient length to enclose the arms of the patient 102 from the shoulders to the wrists. In a supine position, the sleeves 108 are supported by the arms rather than the shoulders. In another embodiment, the sleeves have a longer length such that the hands of the patient 102 are enclosed along in addition to the arms. In such an embodiment, in a supine position, the sleeves 108 are supported by the arms and hands.

The leg portion 112 extends distally toward the feet of the patient 102. In the illustrated embodiment, the leg portion 112 extends to the ankles of the patient 102. In a supine position, the leg portion 112 of the gown 100 is supported by the legs and the lower abdomen.

The drape 106 extending from the leg portion 112 is illustrated in the extended position. The proximal end of the drape 106 is attached to a portion of the hem 116 of the leg portion 112 of the gown 100. In the extended position, the distal end of the drape 106 is detached from the leg portion 112 of the gown 100. The drape 106 extends distally from the hem 116 of the leg portion 112 to beyond the patient's feet. The drape 106 covers and is supported by the patient's feet. The distal end of the drape 106 rests on the bed or other platform supporting the patient 102. With the drape 106 extended beyond the feet, the feet are subject to the warming effects of the gown 100.

On the anterior portion of the leg portion 112 is a slit 402, or opening in the gown 100. The slit 402 is positioned such that it is generally between where the legs of the patient 102 contact the leg portion 112 of the gown 100 with the patient's feet shoulder width apart. The slit 402 provides access to the distributor 206-A from outside the gown 100.

A hose 404 is connected to the proximal end of the distributor 206-A through the slit 402 in the gown 100. The hose 404 provides a gas, such as heated air to the inside of the gown 100 through the distributor 206-A.

Figure 6:
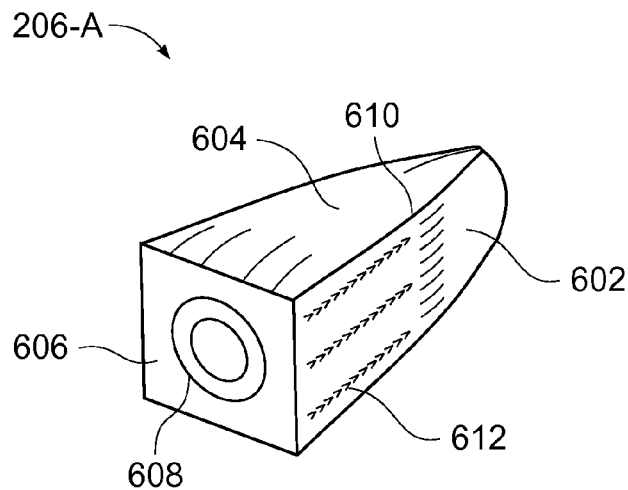
FIG. 6 is a perspective view of one embodiment of a distributor for the warming gown of FIG. 1.
Figure 7:
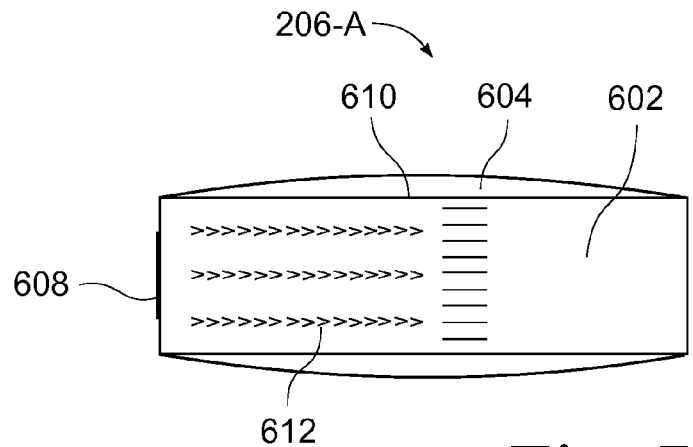
FIG. 7 is a lateral view of the distributor of FIG. 6.
Figure 8:
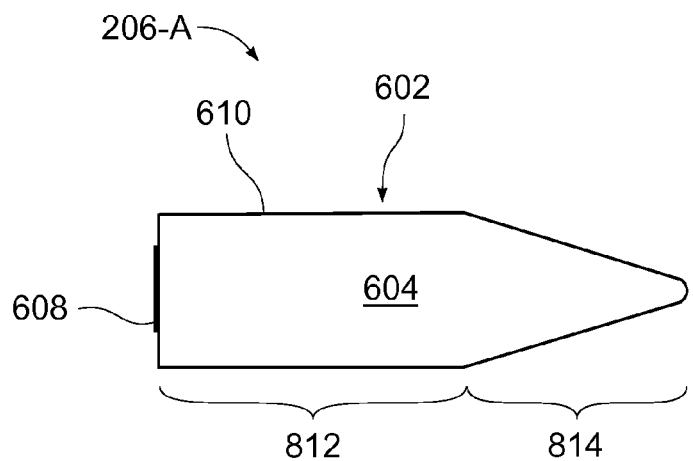
FIG. 8 is an anterior view of the distributor of FIG. 6.

FIG. 6 illustrates a perspective view of one embodiment of a distributor 206-A for the gown 100. FIG. 7 illustrates a lateral view of the distributor 206-A. FIG. 8 illustrates an anterior, or front, view of the distributor 206-A. The distributor 206-A is an elongated device of a general wedge shape. The distributor 206-A includes a base 606 that encloses the proximal end, lateral surfaces 602, and anterior/posterior surfaces 604. In one embodiment, the distributor includes a base 606, two lateral surfaces 602, and corresponding anterior/posterior surfaces 604 that are substantially parallel. It should be noted that the anterior and posterior surfaces 604 are interchangeable. For ease of reference, the anterior surface is described below. The posterior surface is substantially the same except for its location relative to the patient 102.

The base 606 of the distributor 206-A includes a port 608 for receiving a nozzle of a hose 404. The port 608 includes a collar with an opening to receive the nozzle. The port 608 is fastened to the gown at the slit 402 to provide an air tight seal. In one embodiment, the port 608 is fastened to the gown 100 via heat welding. In another embodiment, the port 608 is fastened to the gown 100 via gluing.

The base 606 has edges corresponding to each lateral surface 602 and to each anterior/posterior surface 604. Each of the edges is joined with a lateral surface 602 or an anterior/posterior surface 604 respectively, in alternating fashion. In the illustrated embodiment, two edges join with a lateral surface 602, and two other alternating edges join with an anterior/posterior surface 604.

In one embodiment, each lateral surface 602 is a rectangular portion of fabric extending lengthwise distally from the base of the distributor 206-A. The lateral surfaces 602 oppose each other and extend distally away from the base 606 of the distributor 206-A. The lateral surfaces 602 connect on either edge 610 to an adjacent anterior/posterior surface 604. The distal ends of the lateral surfaces 602 are joined to each other at the distal end of the distributor 206-A. In another embodiment, the lateral surface 602 is a single sheet that wraps around the distal end of the distributor 206-A with the ends of the single sheet connected to the base 610.

Each anterior/posterior surface 604 includes a portion of fabric having a first section 812 near the base 606 and a second section 814 near the distal end of the distributor 206-A. The first section 812 is a substantially rectangular shape that conforms to the shape of the region between the patient's lower legs. The second section 814 is a substantially triangular shape that conforms to the shape of the region between patient's thighs. Each anterior/posterior surface 604 extends lengthwise distally from the base 606 of the distributor 206-A. The anterior/posterior surfaces 604 oppose each other, and are interspersed alternately with the two lateral surfaces 602. Each anterior surface 604 connects on either edge 610 with an adjacent lateral surface 602. Each anterior surface 604 joins the lateral surfaces 602 at the distal end of the respective anterior surface 604. Each lateral surface 602 and each anterior surface 604 has slight curvature away from its respective opposing surface when the distributor 206-A is inflated.

In one embodiment of the distributor 206-A, each of the lateral surfaces 602 includes a plurality of perforations 612. The perforations include triangular, or V-shaped slits in the fabric. This results in a V-shaped flap that allows a gas, such as air, to flow through the flap. In another embodiment, the perforations 612 are openings or holes in the surfaces 602. In yet another embodiment, each of the lateral surfaces 602 is an air permeable material, such as a non-woven fabric or melt blown polypropylene. In another embodiment of the distributor 206-A, each of the lateral surfaces 602 and each of the anterior/posterior surfaces 604 is an air permeable material.

In one embodiment of the distributor 206-A, each of the lateral surfaces 602 and the anterior/posterior surfaces 604 are separate pieces of material that are connected one to another. Each of the sides are connected to the next adjacent side with a substantially air tight seal. For example, the sides are heat welded, glued, sewn, and/or stapled together.

In another embodiment, the distributor 206-A is formed from a single piece of fabric. The single piece of fabric is configured so that each lateral surface 602 is defined by a portion of the single piece of fabric. Similarly each anterior/posterior surface 604 is defined by a portion of the single piece of fabric. The lateral surfaces 602 and the anterior/posterior surfaces 604 are each included within the selfsame single piece of fabric. The distal end of the fabric is formed or cut so as to conform to the shape illustrated in FIGS. 6-8.

The distributor 206-A is oriented within the gown 100 so that the lateral surfaces 602 are between and adjacent to the patient's legs. The anterior and posterior surfaces 604 are oriented toward the forward and rear respectively of the patient 102. When the distributor 206-A is inflated, the lateral surfaces 602 expand toward the patient's legs and the anterior/posterior surfaces 604 expand to the anterior and posterior of the patient. The distributor 206-A inflates with slight curvature of the respective surfaces such that the distributor 206-A is substantially flexible and the patient's legs are not unduly inconvenienced.

The lateral surfaces 602 extend distally from the base 606 in a configuration where the two lateral surfaces 602 are more or less parallel to each other for a portion of the length of the distributor 206-A. This is due to the first section 812 of the anterior/posterior surface 604 which extends from the base 606 to the area near the patient's knees. For the remainder of the length, the lateral surfaces 602 narrow toward each other at the distal end of the distributor 206-A. This is due to the second section 814 of the anterior/posterior surface 604 which extends from the patient's knees to the area near the patient's crotch. The overall length of the lateral surfaces 602 is such that the distributor 206-A extends distally toward the patient's crotch without being uncomfortable for the patient 102. The distributor 206-A narrows at the distal end due to the narrowing of the lateral surfaces 602 toward each other. This allows for the legs of the patient 102 being closer together toward the crotch.

For example, the lateral surfaces 602 are proximate the patient's lower legs in the region corresponding to the first section 812 of the anterior/posterior surfaces 604. The lateral surfaces 602 have a narrowing portion proximate the patient's thighs and corresponding to the second section 814 of the anterior/posterior surfaces 604 to accommodate the narrowing gap in the area from the patient's knees and extending toward the crotch.

The base 606 of the distributor 206-A is attached to the inside anterior surface of the leg portion 112 of the gown 100. The base 606 is attached to the leg portion 112 in the region proximate the slit 402. In one embodiment, the port 608 of the base 606 is secured to the leg portion 112 to form a substantially air tight seal. For example, the port 608 is secured to the leg portion 112 via heat welding, gluing, and/or stapling. With the port 608 secured to the leg portion 112 of the gown 100, the distributor 206-A is accessible via an air hose 404.

In the passive configuration, the distributor 206-A is deflated and rests against the inside anterior surface of the leg portion 112 of the gown 100. The distal end of the distributor 206-A extends toward the patient's crotch. The distal end of the distributor 206-A is attached to the inside anterior surface of the leg portion 112 of the gown 100. In one embodiment, the distal end of the distributor 206-A is tethered to the inside anterior surface of the leg portion 112 in the region proximate the crotch of the patient. In this way, the deflated distributor 206-A is maintained in a manner that does not pose a tripping hazard and also does not impede the mobility of the patient 102. When the distributor 206-A inflates, the tether allows the distributor 206-A to achieve the usual position between the patient's legs. In other embodiments, the distal end of the distributor 206-A is attached to the leg portion 112 via straps, string, hook and loop fasteners, buttons, snaps, and the like.

In another embodiment, the distributor 206-A is a chamber defined by a sheet of an air permeable material that is attached to the lower or leg portion 112 of the gown 100. The sheet of air permeable material is sized to provide air flow to the lower extremities of the patient 102. When the distributor 206-A is deflated, the sheet of air permeable material conforms to the shape of the leg portion 112 of the gown 100. In this way the distributor 206-A is unobtrusive to the patient 102 and the gown 100 has minimal bulk from the distributor 206-A. When inflated, the distributor 206-A assumes a pillow-shape and allows the warming of the lower extremities of the patient by convective air flow and by conduction through the sheet of air permeable material.

Figure 9:
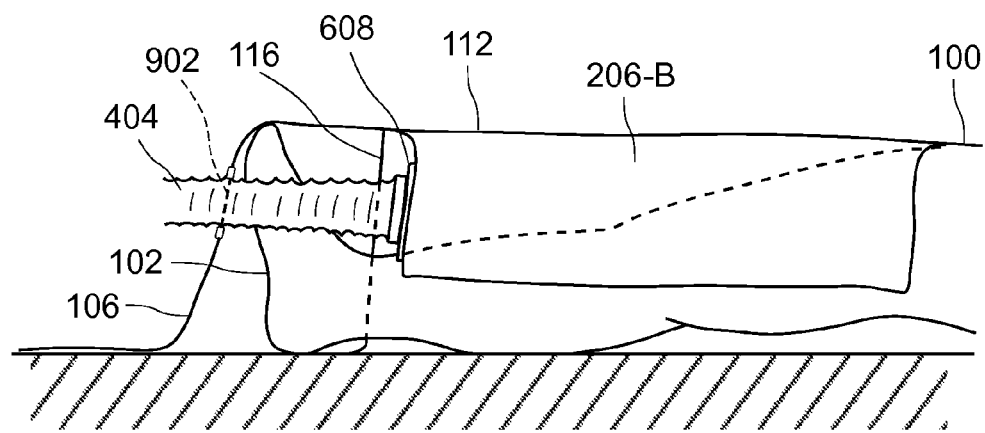
FIG. 9 is a lateral view of a second embodiment of a distributor for the warming gown of FIG. 1.
Figure 10:
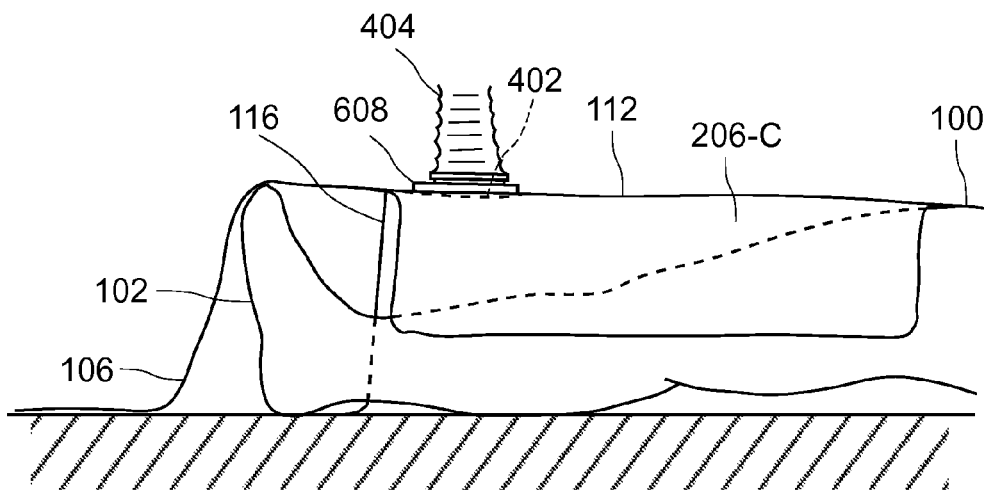
FIG. 10 is a lateral view of a third embodiment of a distributor for the warming gown of FIG. 1.

FIG. 9 illustrates a lateral view of a second embodiment of a distributor 206-B for the gown 100 in which the distributor is accessed through the drape 106 of the gown 100. FIG. 10 illustrates a lateral view of a third embodiment of a distributor 206-C for the gown 100 in which the distributor 206-C is accessed through the front or anterior portion of the gown 100. In the illustrated embodiments of FIG. 9 and FIG. 10, the distributor 206-B, 206-C extends from the region proximate the hem 116 of the gown 100 toward the crotch of the patient 102. In the passive configuration, the distributor 206-B, 206-C is deflated and rests against the inside anterior surface of the leg portion 112 of the gown 100. The proximal and distal ends of the distributor 206-B, 206-C are attached to the inside anterior surface of the leg portion 112. In one embodiment, the proximal end of the distributor 206-B, 206-C is tethered to the inside anterior surface of the leg portion 112 in the region proximate the hem 116.

In FIG. 9, the drape 106 includes a drape slit 902 that is located substantially between the legs of a patient 102 in a supine position with feet shoulder width apart. In the active configuration, the slit 902 is substantially between the feet of the patient 102. The slit 902 provides access to the distributor 206-B.

In the active configuration, the hose 404 extends through the slit 902 in the drape 106 portion of the gown 100. The nozzle of the hose 404 extends between the feet of the patient 102 and is inserted into the port 608 at base 606 of the proximal end of the distributor 206-B.

In FIG. 10, the distributor 206-C is accessed through the slit 402 at the front of the gown 100. As described above (see FIG. 4 and FIG. 5), the slit 402 is positioned substantially between where the legs of the patient 102 contact the leg portion of the gown 100 with the patient's feet shoulder width apart. In another embodiment, the anterior portion of the gown 100 is attached to the distributor 206-C and the port 608 extends from the distributor 206-C through the anterior portion of the gown 100.

The port 608 is located on the anterior surface 604 of the distributor 206-C. In the active configuration, the hose 404 extends through the slit 402 in the leg portion 112 of the gown 100. The nozzle of the hose 404 is inserted into the port 608 on the anterior surface 604 of the distributor 206-C.

Figure 11:
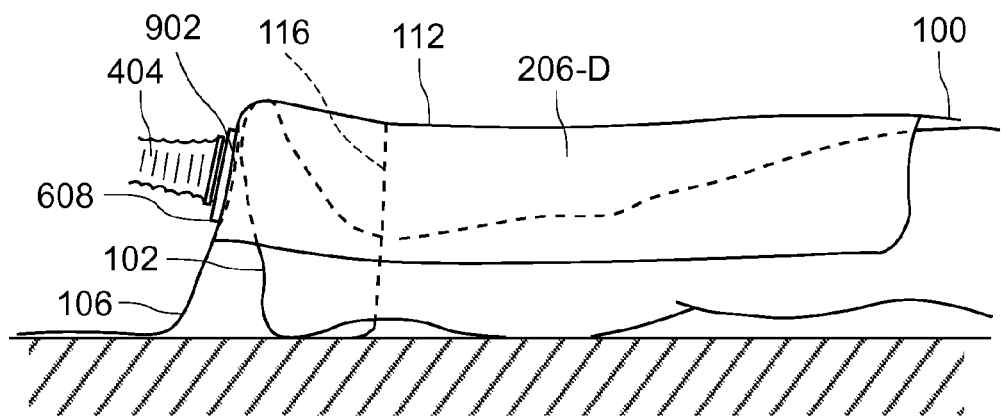
FIG. 11 is a lateral view of a fourth embodiment of a distributor for the warming gown of FIG. 1.

FIG. 11 illustrates a lateral view of a fourth embodiment of a distributor 206-D for the gown 100. In the illustrated embodiment, the distributor 206-D is accessed through the drape 106 of the gown. The distributor 206-D extends from the drape 106, past the feet, between the legs, and toward the crotch area of the patient 102.

In the passive configuration, the distributor 206-D is deflated and rests against a portion of the drape 106 and the inside anterior surface of the leg portion 112 of the gown 100. The base 606 at the proximal end of the distributor 206-D is attached to the inside surface of the drape 106. The distal end of the distributor 206-D is attached to the inside anterior surface of the leg portion 112. In one embodiment, the proximal end of the distributor 206-D is tethered to the inside surface of the drape 106 in the region proximate the hem 116. When the drape is in the stowed position, the deflated distributor 206-D folds or rolls with the drape 106.

As discussed above in FIG. 9, the drape 106 includes a drape slit 902 that is located substantially between the legs of a patient 102 in a supine position with feet shoulder width apart. In the active configuration, the slit 902 is substantially between the feet of the patient 102. The slit 902 provides access to the distributor 206-D. In the active configuration, the nozzle of the hose 404 extends through the slit 902 of the drape 106 and is inserted into the port 608 at the proximal end of the distributor 206-D. In another embodiment, the port 608 extends from the base 606 of the distributor 206-D through the drape 106, with the base 606 attached to the drape 106.

Figure 12:
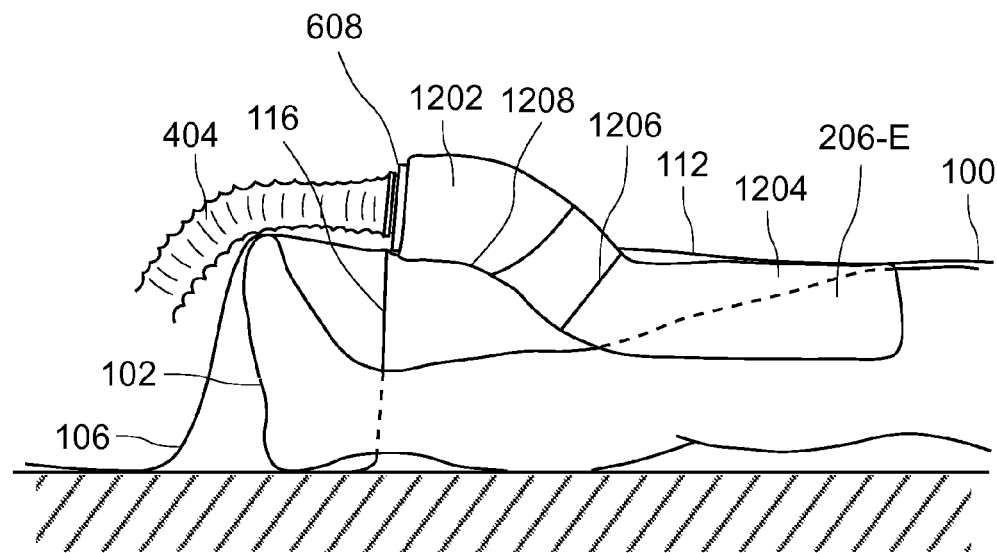
FIG. 12 is a lateral view of a fifth embodiment of a distributor for the warming gown of FIG. 1.

FIG. 12 illustrates a lateral view of a fifth embodiment of a distributor 206-E for the gown 100. In the illustrated embodiment, the distributor 206-E has a first section 1202 and a second section 1204 joined at a seam 1206. The first section 1202 is substantially external to the gown 100 and is not air permeable. The second section 1204 is internal to the gown 100 and is air permeable.

The proximal end of the first section 1202 of the distributor 206-E is attached to the outside anterior surface of the leg portion 112 proximate the hem 116 of the gown 100. The first section 1202 of the distributor 206-E extends through a slit 1208 to the inside of the gown 100. The slit 1208 is located proximate the hem 116 in the leg portion 112 of the gown 100 and is positioned substantially between where the legs of the patient 102 contact the leg portion of the gown 100 with the patient's feet shoulder width apart. The second section 1204 of the distributor 206-E is located within the gown 100 and extends from the seam 1206 toward the crotch of the patient 102.

In the passive configuration, the distributor 206-E is deflated and rests partially against the inside and partially against the outside anterior surfaces of the leg portion 112 of the gown 100. The distal end of the second section 1204 of the distributor 206-E is attached to the inside anterior surface of the leg portion 112. In one embodiment, the distal end of the second section 1204 of the distributor 206-E is tethered to the inside anterior surface of the leg portion 112. When the drape 106 is in the stowed position, the first section 1202 is covered by the drape 106.

In the active configuration, the nozzle of the hose 404 is inserted into the port 608 of the first section 1202 of the distributor 206-E. In one embodiment, the hose 404 rests upon the feet of the patient 102. Such an embodiment, provides for a distribution of the weight of the hose 404 and distributor 206-E and minimizes stresses upon the toes of the patient 102.

Figure 13:
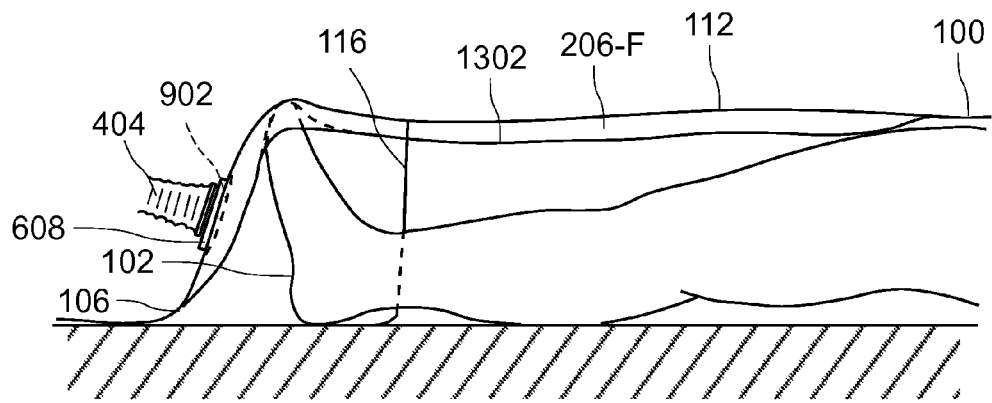
FIG. 13 is a lateral view of a sixth embodiment of a distributor for the warming gown of FIG. 1.

FIG. 13 illustrates a lateral view of a sixth embodiment of a distributor 206-F for the gown 100. In the illustrated embodiment, the gown 100 includes an inner layer 1302 adjacent the drape 106 and the leg portion 112. The inner layer 1302 is air permeable. The peripheral edge of the inner layer 1302 is joined to the drape 106 and the leg portion 112 of the gown 100, which are not air permeable, to create a distributor or chamber 206-F. The inner layer 1302 is joined to the drape 106 proximate the distal end of the drape 106. The inner layer 1302 extends toward the waist of the patient 102. In one embodiment, the inner layer 1302 is joined to the leg portion 112 proximate the crotch area of the patient 102. In one embodiment, the chamber 206-F is between the legs of the patient 102, and extends from the region proximate the distal end of the drape 106 towards the crotch area of the patient 102. In another embodiment, the distributor 206-F has a width that extends past the legs of the patient 102 such that the distributor 206-F covers the lower extremities of the patient 102.

In the illustrated embodiment, the chamber 206-F is accessed through the drape 106 of the gown. The chamber 206-F extends from the drape 106, past the feet, between the legs, and toward the crotch area of the patient 102. In the passive configuration, the chamber 206-F is deflated and the inner layer 1302 rests against a portion of the drape 106 and the inside anterior surface of the leg portion 112 of the gown 100. When the drape is in the stowed position, the deflated chamber 206-F folds or rolls with the drape 106.

As discussed above in FIG. 9, the drape 106 includes a drape slit 902 that is located substantially between the legs of a patient 102 in a supine position with feet shoulder width apart. In the active configuration, the slit 902 is substantially between the feet of the patient 102. The slit 902 provides access to the chamber 206-F. In the active configuration, the nozzle of the hose 404 extends through the slit 902 of the drape 106 and is inserted into the port 608 that is joined to the chamber 206-F.

Figure 14:
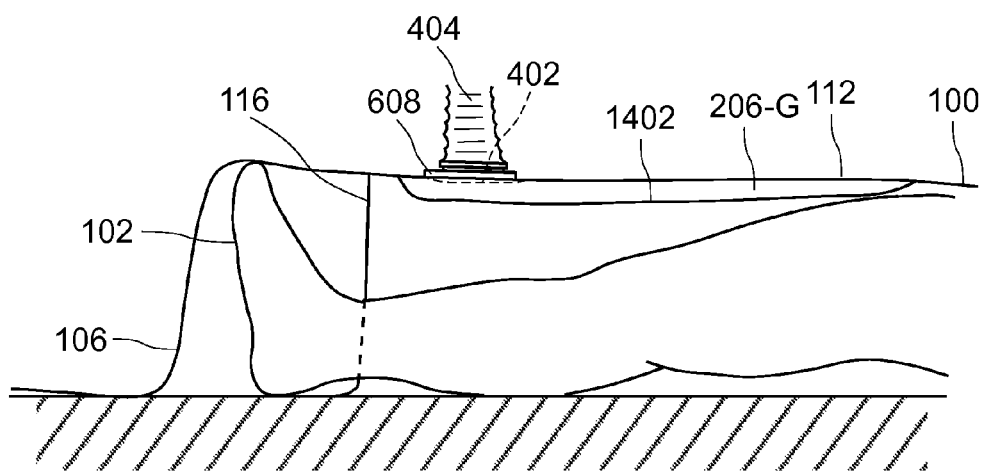
FIG. 14 is a lateral view of a seventh embodiment of a distributor for the warming gown of FIG. 1.

FIG. 14 illustrates a lateral view of a seventh embodiment of a distributor 206-G for the gown 100. In the illustrated embodiment, the gown 100 includes an inner layer 1402 adjacent the leg portion 112. The inner layer 1402 is air permeable. The peripheral edge of the inner layer 1402 is joined to the leg portion 112 of the gown 100 to create a distributor or chamber 206-G. A portion of the leg portion 112 of the gown, which is not air permeable, forms an outer layer of the chamber 206-G. The inner layer 1402 is joined to the leg portion 112 proximate the hem 116 of the gown 100. The inner layer 1402 extends toward the waist of the patient 102. In one embodiment, the inner layer 1402 is joined to the leg portion 112 proximate the crotch area of the patient 102. In one embodiment, the chamber 206-G is between the legs of the patient 102, and extends from the region proximate the hem 116 towards the crotch area of the patient 102.

In the illustrated embodiment, the chamber 206-G is accessed through the slit 402 at the front of the gown 100. The slit 402 is positioned substantially between where the legs of the patient 102 contact the leg portion of the gown 100 with the patient's feet shoulder width apart. In another embodiment, the anterior portion of the gown 100 is attached to the distributor 206-G and the port 608 extends from the distributor 206-G through the anterior portion of the gown 100.

In the illustrated embodiment, the port 608 is proximate the slit 402 and located on the anterior surface of the leg portion 112 of the gown 100. In the active configuration, the hose 404 extends through the slit 402 in the leg portion 112 of the gown 100. The nozzle of the hose 404 is inserted into the port 608 on the anterior surface of the leg portion 112 which is an outer layer of the chamber 206-G. In the passive configuration, the chamber 206-G is deflated and the inner layer 1402 rests against the inside anterior surface of the leg portion 112 of the gown 100.

In operation, a patient 102 is outfitted with a gown 100 prior to surgery or some other medical procedure. This typically occurs with the patient in a standing position. The flaps 204 are joined to close the posterior opening 202 of the gown. The drape 106 is stowed in the stored position. A hose 404 is not connected to the distributor 206-A. The distributor 206-A is deflated and positioned substantially adjacent the anterior portion of the leg portion 106. In the standing position, the patient 102 is free to walk around or sit as the need arises while waiting for the procedure to begin.

When the patient 102 first puts the gown 100 on, the gown 100 is in the mobile configuration. In this configuration, the gown's passive heating comes into play. The reflective material of the sleeves 108, leg portion 112, and posterior thorax portion 110 reduce the loss of the body heat of the patient 102. The anterior thorax portion 110 has no heat reflective material and the body heat generated by the patient's torso is radiated through the anterior thorax portion 110. In this way, the gown 100 prevents redistribution hypothermia when the patient 102 is mobile.

For the procedure, the patient 102 is typically situated in either a supine, prone, or Fowler's position. For illustration purposes, the patient 102 is discussed in a supine position on a gurney. The drape 106 is detached from the leg portion 112 of the gown 100. The drape 106 is extended to cover the feet of the patient 102 with the distal end of the drape 106 resting on the gurney. The nozzle of a hose 404 is inserted through the slit 402 and into the inlet port 608 of the distributor 206-A. Heated, forced air is generated by a blower attached to the hose 404. To prevent unintended cooling of the patient 102, the temperature of the air from the blower is typically adjusted to a range from 36-43° C.

The heated, forced air enters the distributor 206-A from the hose 404. As the heated, forced air enters the distributor 206-A, the air pressure inside the distributor 206-A increases causing the distributor 206-A to inflate whereby the lateral surfaces 602 and the anterior surfaces 604 move apart. The heated air is exhausted through the surfaces of the distributor 206-A and into the remainder of the gown 100.

In the active configuration, the gown 100 provides active heating through the distributor 206-A and passive heating by the reflective material. The heated air flows through the distributor 206-A and throughout the remaining portions of the gown 100. Since the drape 106, the sleeves 108, the leg portion 112, and the posterior portion of the body 104 all include a heat reflective material, radiation loss of the heat is reduced. Loss of heat at the back and at the extremities is reduced. Some heated air leaves the gown gradually through the neck opening 114, the ends of the sleeves 108, the posterior opening 202, and the edges of the drape 106.

The anterior region of the thorax portion 110 of the gown 100 has no heat reflective properties. The thorax, or chest, region of the patient 102 does not experience as much warming since the heat is allowed to escape through the thorax portion of the gown 100. In this way, the core temperature of the patient 102 is not increased unnecessarily.

Heated air is provided to the inside of the gown 100 through the distributor 206-A. Air temperature is maintained at a desired level for the extremities, while also preventing the chest or anterior thorax from being raised to an uncomfortable level. The air temperature of the patient 102 is maintained within the gown 100 before, during, and/or after surgery or any other medical procedure.

Figure 15:
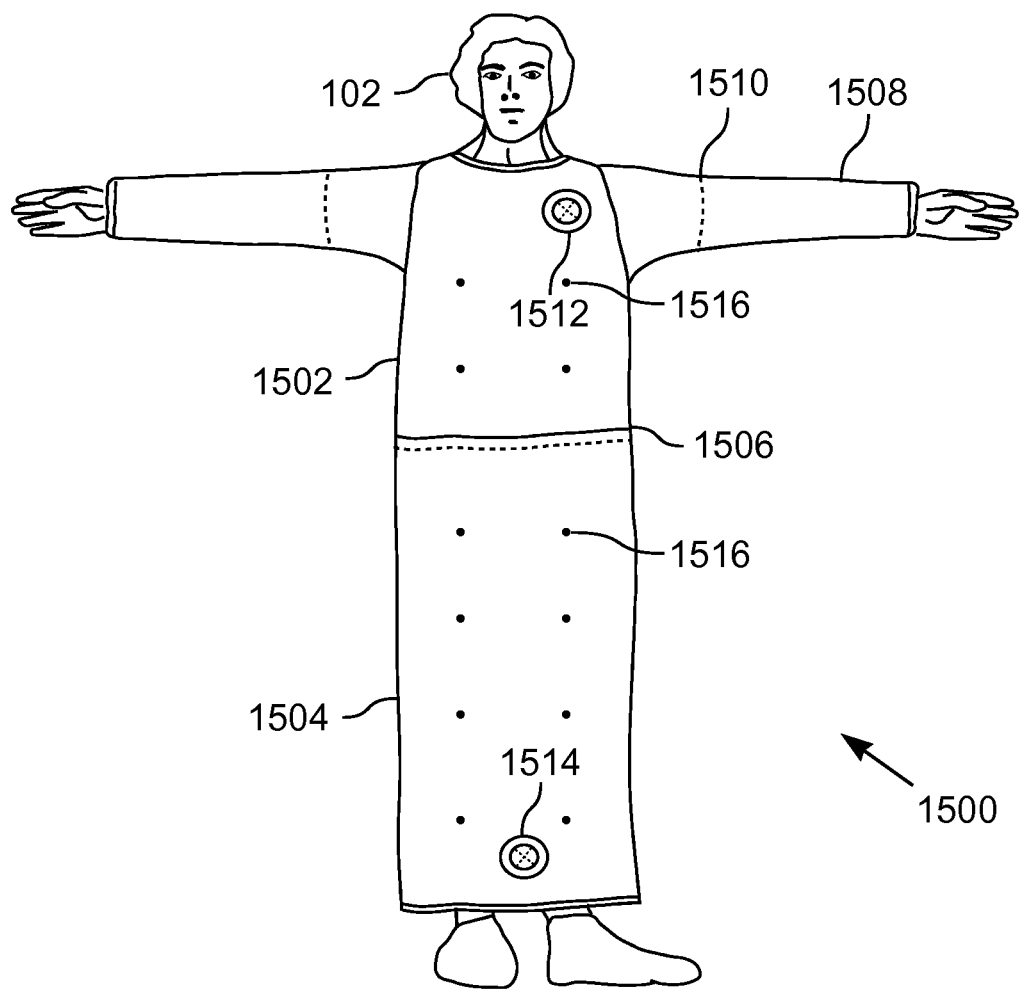
FIG. 15 is a front view of a patient wearing one embodiment of the prewarming gown.

FIG. 15 illustrates a front view of a patient 102 wearing one embodiment of the prewarming gown 1500. The prewarming gown 1500 is a garment configured to cover a substantial portion of a patient 102. The prewarming gown 1500 provides passive warming by nature of its multi-layer construction covering the patient 102. The prewarming gown 1500 provides active warming by the integral inflatable air chambers that provide convective warming.

The prewarming gown 1500 has an upper body portion 1502 and a lower body portion 1504. The lower body portion 1504 is releasably attached to the upper body portion 1502 with a releasable and reattachable mechanism 1506, for example, a hook and loop fastening system. Each of the upper body portion 1502 and the lower body portion 1504 has an air inlet 1512, 1514 that allows connection of an air supply hose when the prewarming gown 1500 is used for active warming of the patient 102.

The upper body portion 1502 is a garment configured to be worn on the upper body of the patient 102. The upper body portion 1502 has a main body part and two sleeves 1508. In the illustrated embodiment, the sleeves 1508 are separable from the remainder of the upper body portion 1502. A seam 1510 near the shoulder allows each sleeve 1508 to be removed. In one embodiment the seam 1510 is a perforation that allows the sleeve 1508 to be removed. In other embodiments the seam 1510 includes snaps or a hook and loop fastening system that allows the sleeve 1508 to be removed and replaced as desired.

The lower body portion 1504 has an attachment mechanism 1506 that connects the lower body portion 1504 to the upper body portion 1502. In one embodiment the attachment mechanism 1506 is a perforation that allows the lower body portion 1504 to be separated from the upper body portion 1502. In other embodiments the attachment mechanism 1506 includes snaps or a hook and loop fastening system that allows the lower body portion 1504 to be removed and replaced as desired. In one embodiment, the length, or width, of the bottom of the upper body portion 1502 is substantially equal to the length, or width, of the top of the lower body portion 1504 such that the bottom and top mate at the attachment mechanism 1506 to form a gown that extends to the inferior position all the way around the patient 102. In another embodiment, the length of the top of the lower body portion 1504 is less than the length of the bottom of the upper body portion 1502 whereby the lower body portion 1502 does not completely wrap around the legs of the patient 102.

In one embodiment, the lower body portion 1504 includes a plurality of connections 1516 that prevent the lower body portion 1504 from ballooning out. As illustrated below, the lower body portion 1504 is formed from an outer sheet 1602 and an inner sheet 1604 that form an inflatable chamber. The connections 1516 prevent that chamber from expanding into a pillow-shape by keeping the two sheets 1602, 1604 connected at several locations inside the perimeter of the sheets 1602, 1604.

Figure 16:
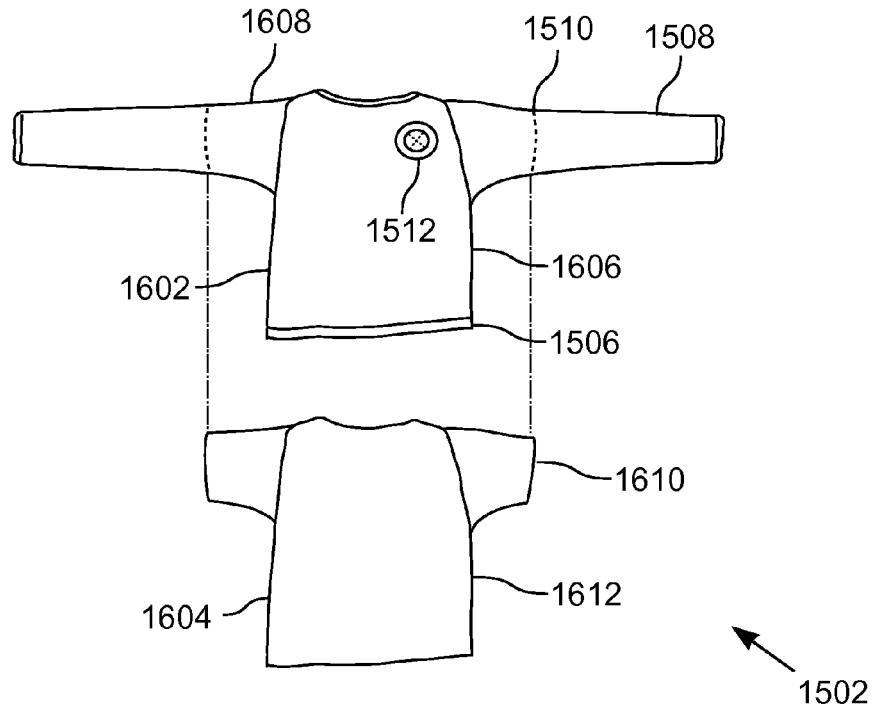
FIG. 16 is an exploded view of one embodiment of the upper body portion of the prewarming gown.

FIG. 16 illustrates an exploded view of one embodiment of the upper body portion 1502 of the prewarming gown 1500. The upper body portion 1502 includes an outer sheet 1602 and an inner sheet 1604 that form an inflatable chamber. The outer sheet 1602 is configured as a gown with a thorax portion 1606. The upper body portion 1502 has a posterior opening 202 that divides the thorax portion 1606 vertically so that the patient 102 can don the upper body portion 1502.

The sleeves 1508 have a seam, or connection, 1510 that joins each of the long sleeves 1508 to a short sleeve 1608 that is attached to the thorax portion 1606 of the outer sheet 1602. The inner sheet 1604 has corresponding short sleeves 1610 that fit inside the short sleeves 1608 of the outer sheet 1602. The inner sheet 1604 has a corresponding thorax portion 1612 that fits inside the thorax portion 1606 of the outer sheet 1602. The peripheral edges of the outer sheet 1602 are connected to the inner sheet 1604 with an air-tight bond.

In another embodiment, the inner sheet 1604 has a smaller size than the outer sheet 1602. For example, the inner sheet 1604 has no short sleeves 1610 and/or the thorax portion 1612 does not extend downward as far as the thorax portion 1606 of the outer sheet 1602. In such an embodiment, the inner sheet 1604 is connected to the outer sheet 1602 at the perimeter, or peripheral edge, of the inner sheet 1604. In one such embodiment, the inner sheet 1604 is dimensioned to fit adjacent the anterior part of the thorax portion 1606 between the lower hem and the neck opening. In this way the inflatable chamber is adjacent only the anterior thorax of the patient 102. In such an embodiment the posterior part of the outer sheet 1602 is an air permeable material that allows the air exhausted from the inflatable chamber to further exhaust through the posterior of the upper body portion 1502 of the prewarming gown 1500.

In addition to the peripheral connection of the inner sheet 1604 to the outer sheet 1602, the inner sheet 1604 and the outer sheet 1602 are joined by connections 1516 away from the peripheral edge. The connections 1516 prevent the outer and inner sheets 1602, 1604 from being forced apart from each other and subsequently forming a large pillow. The connections 1516 allow the upper body portion 1502 to form an inflated blanket with a limited thickness.

The outer sheet 1602 is an air impermeable material and forms the outer surface of the upper body portion 1502 of the prewarming gown 1500. The outer sheet 1602 has a width sufficient to wrap around the lower body of the patient 102. In one embodiment, a pair of straps 208 are secured to the upper body portion 1502, such as depicted in FIG. 2. The straps 208 allow the posterior portion of the upper body portion 1502 to be fastened together when the prewarming gown 1500 is worn. In other embodiments, buttons, snaps, a hook and loop fastener system, or other fastening mechanism is used in lieu of the straps 208.

The outer sheet 1602 has an opening with a stiffening ring for the inlet 1512. In one embodiment, the opening includes one or more perforations that are broken when an air supply nozzle is inserted in the opening. Those skilled in the art will recognize that the inlet 1612 is configured to allow mating with an air supply nozzle for supplying conditioned air to the upper body portion 1502 of the prewarming gown 1500.

In one embodiment the outer sheet 1602 has portions that have heat reflective properties. When the upper body portion 1502 is used in a passive warming mode, the heat reflective properties of the outer sheet 1602 help maintain the body temperature of selected portions of the patient 102 that are covered with the heat reflective portions of the outer sheet 1602. In one such embodiment, the long sleeves 1508, the short sleeves 1608, and the anterior part of the thorax portion 1606 are heat reflective. The posterior part of the thorax portion 1606 is not heat reflective. In various embodiments heat reflection is obtained by a coating on the surface or by using a material that inherently is heat reflective. For example, an aluminized layer bonded to a substrate is heat reflective.

The inner sheet 1604 is an air permeable material and forms the inside surface of the upper body portion 1502 of the prewarming gown 1500. In one embodiment the inner sheet 1604 is a non-woven material that is porous and allows the passage of pressurized air. In other embodiments the inner sheet 1604 is perforated or has a plurality of openings or slits through which air escapes.

Figure 17:
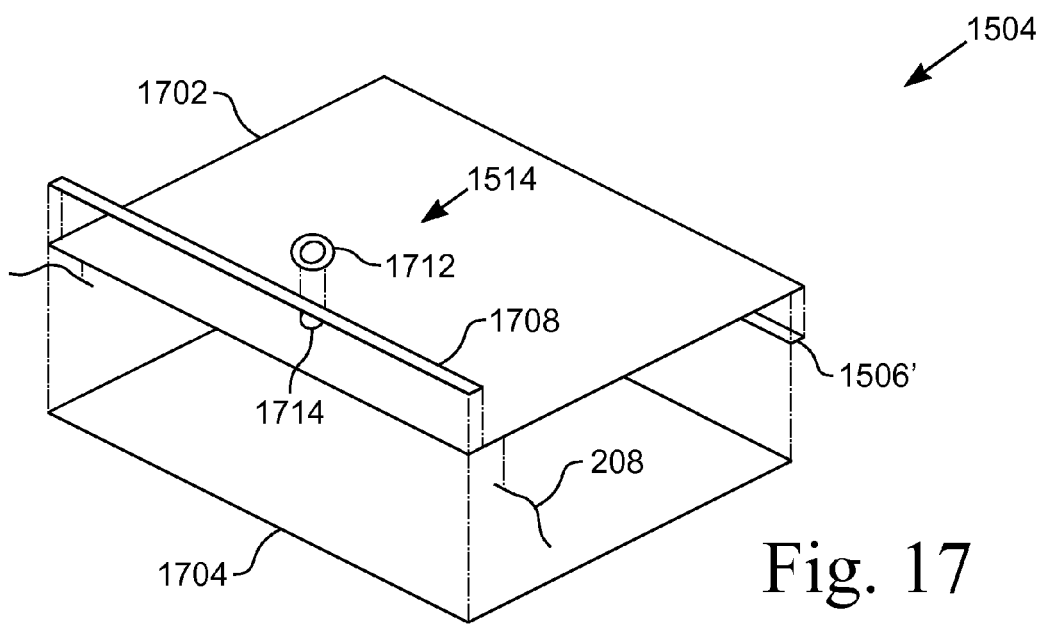
FIG. 17 is an exploded view of one embodiment of the lower body portion of the prewarming gown.

FIG. 17 illustrates an exploded view of one embodiment of the lower body portion 1504 of the prewarming gown 1500. The lower body portion 1504 includes an outer sheet 1702 and an inner sheet 1704 that are connected at their peripheral edges with an air-tight bond to form an inflatable chamber. In another embodiment, the inner sheet 1704 is dimensionally smaller than the outer sheet 1702. In such an embodiment, the inner sheet 1704 is connected to the outer sheet 1702 at the perimeter, or peripheral edge, of the inner sheet 1704. In one such embodiment, the inner sheet 1704 is dimensioned to be adjacent the anterior part of the lower body portion 1504 of the prewarming gown 1500. Additionally, the posterior part of the outer sheet 1702 is an air permeable material that allows the air exhausted from the inflatable chamber to further exhaust through the posterior of the lower body portion 1504 of the prewarming gown 1500.

In addition to the perimeter connection of the inner sheet 1704 to the outer sheet 1702, the inner sheet 1704 and the outer sheet 1702 have connections 1516 away from the perimeter. The connections 1516 prevent the outer and inner sheets 1702, 1704 from being forced apart from each other and subsequently forming a large pillow. The connections 1516 allow the lower body portion 1504 to form an inflated blanket.

The outer sheet 1702 is an air impermeable material and forms the outer surface of the lower body portion 1504 of the prewarming gown 1500. The outer sheet 1702 has a width sufficient to wrap around the lower body of the patient 102. In the illustrated embodiment, a pair of straps 208 are secured to the outer sheet 1702. The straps 208 allow the posterior portion of the lower body portion 1504 to be fastened together when the prewarming gown 1500 is worn. In other embodiments, buttons, snaps, a hook and loop fastener system, or other fastening mechanism is used in lieu of the straps 208.

The outer sheet 1702 has an opening 1714 that forms part of the inlet 1514. In one embodiment, the opening 1714 includes one or more perforations that are broken when an air supply nozzle is inserted in the opening 1714. A stiffening ring 1712 is secured around the opening 1714 as another part of the inlet 1514. Those skilled in the art will recognize that the inlet 1714 is configured to allow mating with an air supply nozzle for supplying conditioned air to the lower body portion 1504 of the prewarming gown 1500.

In one embodiment the outer sheet 1702 has portions with heat reflective properties. When the lower body portion 1504 is used in a passive warming mode, the heat reflective properties of the outer sheet 1702 help maintain the body temperature of the portion of the patient 102 that is covered. In another embodiment, the anterior part of the outer sheet 1702 is covered with heat reflective material and the posterior part of the outer sheet 1702 is not covered with heat reflective material.

One half of a hook and loop fastening system 1506' is attached to the upper end of the outer sheet 1702. The mating half of the hook and loop fastening system 1506 is attached to the lower part of the upper body portion 1502. In this way the upper body portion 1502 and the lower body portion 1504 are releasably connectable. In another embodiment, the upper body portion 1502 and the lower body portion 1504 are attached with a perforated connection or a weakened line that is susceptible to tearing to separate the lower portion 1504 from the upper portion 1502. In yet other embodiments, the lower portion 1504 is connected to the upper portion 1502 by snaps, buttons, tape, or other releasable connections.

The illustrated embodiment shows a double-sided tape strip 1708 attached to the lower edge of the lower body portion 1504 of the prewarming gown 1500. The tape strip 1708 has a protective cover that is removable to expose the adhesive. The tape strip 1708 is positioned to allow the lower portion 1504 to be secured to the upper portion 1502, such as when the lower body of the patient 102 is desired to be exposed. In another embodiment, the tape strip 1708 is attached to the upper portion 1502.

The inner sheet 1704 is an air permeable material and forms the inside surface of the lower body portion 1504 of the prewarming gown 1500. In one embodiment the inner sheet 1704 is a non-woven material that is porous and allows the passage of pressurized air. In other embodiments the inner sheet 1704 is perforated or has a plurality of openings or slits through which air escapes.

The prewarming gown 1500 is a multipurpose garment. During the pre-operative phase, the patient 102 wears the prewarming gown 1500 with the upper body portion 1502 attached to the lower body portion 1504. The prewarming gown 1500 passively warms the patient by virtue of the two layers of material 0602, 1604, 0702, 0704 and the portions of the prewarming gown 1500 that are heat reflective. For active warming, a warm air blower is connected to the inlet 1514 of the lower body portion 1504.

During transport to the operating room, the patient 102 continues to wear the prewarming gown 1500 with the upper body portion 1502 attached to the lower body portion 1504. The prewarming gown 1500 passively warms the patient by virtue of the two layers of material 0602, 1604, 0702, 0704 and the portions of the prewarming gown 1500 that are heat reflective.

When the patient 102 is in the operating room, the prewarming gown 1500 is adjusted to fit the requirements of the medical staff. For example, a warm air blower is connected to the inlet 1512 of upper body portion 1502 and the lower body portion 1504 is removed at the connection 1506 or left in place. Another example is the lower body portion 1504 is connected to a warm air blower and the upper body portion 1502 is removed at the connection 1506 or left in place. Yet another example is the prewarming gown 1500 is removed from the patient 102 and positioned over the patient 102 as a warming blanket with a warm air blower connected to one or both of the inlets 1512, 1514. Alternatively, the upper body portion 1502 is separated from the lower body portion 1504 at the connection 1506 and either the upper body portion 1502 or the lower body portion 1504 is used individually to warm the patient 102 with a warm air blower connected to the appropriate inlet 1512, 1514.

For transport from the operating room, both the upper body portion 1502 and the lower body portion 1504 are connected together and the prewarming gown 1500 provides passive warming as described above when being transported to the operating room.

For the post-operative or recovery period, the prewarming gown 1500 provides either passive warming or active warming by connecting a warm air supply to one or both of the inlets 1512, 1514.

From the foregoing description, it will be recognized by those skilled in the art that systems and methods for actively warming patients while passively reducing radiation heat loss has been provided. The systems and methods can be used before, during, or after surgery without departing from the spirit and scope of the present invention.

While the present invention has been illustrated by description of several embodiments and while the illustrative embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicant's general inventive concept.

What is claimed is:

1. An apparatus for providing temperature control of a patient, said apparatus comprising:
   a first sheet defining a thorax portion and a pair of sleeves, said first sheet having an inside surface that is proximate the patient when the patient is wearing said first sheet;
   a second sheet having a periphery attached to said first sheet with an air tight seal, said first sheet and said second sheet defining a first chamber between said second sheet and a portion of said first sheet proximate said second sheet, said second sheet being air impermeable, said portion of said first sheet being air permeable, said first and second sheets defining an upper body portion;
   a first inlet defined by a passage in said second sheet into said first chamber, said first inlet configured to connect with an air hose;
   a third sheet having an inside surface that is proximate the patient when the patient is wearing said third sheet;
   a fourth sheet having a periphery attached to said third sheet with an air tight seal, said third sheet and said fourth sheet defining a second chamber between said fourth sheet and a portion of said third sheet proximate said fourth sheet, said fourth sheet being air impermeable, said portion of said third sheet being air permeable, said third and fourth sheets defining a lower body portion which is configured to wrap completely around the legs of the patient when the patient is wearing said lower body portion;
   a second inlet defined by a passage in said fourth sheet into said second chamber, said second inlet configured to connect with said air hose;
   a connector releasably joining a bottom of said upper body portion and a top of said lower body portion; and
   a plurality of connections between said third sheet and said fourth sheet, said plurality of connections distributed inside a boundary defined by a peripheral edge of said fourth sheet whereby said third sheet is constrained to expand a limited distance from said fourth sheet when said second chamber is inflated with air.

2. The apparatus of claim 1 wherein said bottom of said upper body portion is proximate a pelvis of the patient when the patient is wearing said upper body portion.

3. The apparatus of claim 1 wherein said lower body portion has a length wherein a bottom of said lower body portion is proximate a foot of the patient when the patient is wearing said lower body portion with said lower body portion joined with said upper body portion.

4. The apparatus of claim 1 wherein said first chamber is dimensioned to be proximate an anterior portion of said upper body portion, and said anterior portion corresponding to a position proximate an anterior thorax of the patient when the patient is wearing said upper body portion.

5. The apparatus of claim 1 wherein said first chamber is dimensioned to extend into a portion of said pair of sleeves proximate said thorax portion.

6. The apparatus of claim 1 further including a seam between a medial portion and a distal portion of each sleeve wherein said distal portion of each one of said pair of sleeves is separable from said medial portion of said each one of said pair of sleeves.

7. The apparatus of claim 1 wherein said second chamber is dimensioned to be proximate an anterior portion of the lower body of the patient when said upper body portion is connected to said lower body portion and the patient is wearing said upper body portion and said lower body portion.

8. The apparatus of claim 1 wherein said pair of sleeves and an anterior portion of said upper body portion are heat reflective.

9. The apparatus of claim 1 wherein an anterior portion of said third sheet is heat reflective and a posterior portion of said third sheet is not heat reflective.

10. The apparatus of claim 1 wherein a posterior portion of said upper body portion and a posterior portion of said lower body portion are air permeable.

11. The apparatus of claim 1 wherein said third sheet has a top edge with a length substantially equal to a length of a bottom edge of said first sheet.

12. The apparatus of claim 1, further comprising a fifth sheet attached to the lower body portion and configured to cover the patient's feet.

13. The apparatus of claim 12, wherein the fifth sheet is configured to cover the patient's feet by extending over and beyond the patient's feet when the patient is in a prone position.

14. An apparatus for providing temperature control of a patient, said apparatus comprising:
   a first sheet defining a thorax portion and a pair of sleeves, said first sheet having an inside surface that is proximate the patient when the patient is wearing said first sheet;
   a second sheet having a periphery attached to said first sheet with an air tight seal, said first sheet and said second sheet defining a first chamber between said second sheet and a portion of said first sheet proximate said second sheet, said second sheet being air impermeable, said portion of said first sheet being air permeable, said first and second sheets defining an upper body portion;
   a first inlet defined by a passage in said first sheet into said first chamber, said first inlet configured to connect with an air hose;
   a third sheet having an inside surface that is proximate the patient when the patient is wearing said third sheet;
   a fourth sheet having a periphery attached to said third sheet with an air tight seal, said third sheet and said fourth sheet defining a second chamber between said fourth sheet and a portion of said third sheet proximate said fourth sheet, said fourth sheet being air impermeable, said portion of said third sheet being air permeable, said third and fourth sheets defining a lower body portion which is configured to wrap completely around the legs of the patient between the patient's knees and ankles when the patient is wearing said lower body portion and said sleeves;

a second inlet defined by a passage in said third sheet into said second chamber, said second inlet configured to connect with said air hose;

a connector releasably joining a bottom of said upper body portion and a top of said lower body portion; and a plurality of connections between said third sheet and said fourth sheet, said plurality of connections distributed inside a boundary defined by a peripheral edge of said fourth sheet whereby said third sheet is constrained to expand a limited distance from said fourth sheet when said second chamber is inflated with air.

15. An apparatus for providing temperature control of a patient, said apparatus comprising:

a first sheet defining a thorax portion and a pair of sleeves, said first sheet having an inside surface that is proximate the patient when the patient is wearing said first sheet;

a second sheet having a periphery attached to said first sheet with an air tight seal, said first sheet and said second sheet defining a first chamber between said second sheet and a portion of said first sheet proximate said second sheet, said second sheet being air impermeable, said portion of said first sheet being air permeable, said first and second sheets defining an upper body portion;

a first inlet defined by a passage in said first sheet into said first chamber, said first inlet configured to connect with an air hose;

a third sheet having an inside surface that is proximate the patient when the patient is wearing said third sheet;

a fourth sheet having a periphery attached to said third sheet with an air tight seal, said third sheet and said fourth sheet defining a second chamber between said fourth sheet and a portion of said third sheet proximate said fourth sheet, said fourth sheet being air impermeable, said portion of said third sheet being air permeable, said third and fourth sheets defining a lower body portion;

a fifth sheet attached to the lower body portion and configured to cover the patient's feet;

a second inlet defined by a passage in said third sheet into said second chamber, said second inlet configured to connect with said air hose;

a connector releasably joining a bottom of said upper body portion and a top of said lower body portion; and a plurality of connections between said third sheet and said fourth sheet, said plurality of connections distributed inside a boundary defined by a peripheral edge of said fourth sheet whereby said third sheet is constrained to expand a limited distance from said fourth sheet when said second chamber is inflated with air.

* * * * *